(12) United States Patent
Rovatti et al.

(10) Patent No.: US 7,935,258 B2
(45) Date of Patent: May 3, 2011

(54) PROCESS AND AN APPARATUS FOR FILLING AND/OR RINSING AN EXTRACORPOREAL BLOOD CIRCUIT

(75) Inventors: Paolo Rovatti, Finale Emilia (IT); Matteo Paltrinieri, Medolla (IT)

(73) Assignee: Gambro Lundia AB, Lund (SE)

( * ) Notice: Subject to any disclaimer, the term of this patent is extended or adjusted under 35 U.S.C. 154(b) by 490 days.

(21) Appl. No.: 12/066,067

(22) PCT Filed: Sep. 15, 2005

(86) PCT No.: PCT/IB2005/002735
§ 371 (c)(1),
(2), (4) Date: Mar. 6, 2008

(87) PCT Pub. No.: WO2007/031809
PCT Pub. Date: Mar. 22, 2007

(65) Prior Publication Data
US 2008/0237128 A1    Oct. 2, 2008

(51) Int. Cl.
*B01D 61/30* (2006.01)
*B01D 61/28* (2006.01)
*B01D 61/00* (2006.01)
*B01D 65/00* (2006.01)

(52) U.S. Cl. .......... 210/636; 210/646; 210/650

(58) Field of Classification Search .......... 210/636, 210/645, 646, 650, 97, 103, 104, 134, 143, 210/252, 257.2, 258, 321.69, 427, 436, 472
See application file for complete search history.

(56) References Cited

U.S. PATENT DOCUMENTS

| | | | |
|---|---|---|---|
| 4,324,662 A | 4/1982 | Schnell | |
| 5,259,961 A | 11/1993 | Eigendorf | |
| 5,650,071 A | 7/1997 | Brugger et al. | |
| 5,776,091 A | 7/1998 | Brugger et al. | |
| 5,863,421 A | 1/1999 | Peter, Jr. et al. | |
| 5,895,368 A | 4/1999 | Utterberg et al. | |
| 6,132,616 A | 10/2000 | Twardowski et al. | |
| 6,277,272 B1 | 8/2001 | Nikaido et al. | |
| 6,290,665 B1 | 9/2001 | Utterberg | |
| 6,331,252 B1 | 12/2001 | El Sayyid et al. | |
| 2003/0163077 A1* | 8/2003 | Kim et al. | 604/5.1 |
| 2004/0149656 A1* | 8/2004 | Rovatti | 210/636 |

FOREIGN PATENT DOCUMENTS

| | | |
|---|---|---|
| DE | 34 42 744 A1 | 6/1986 |
| DE | 100 11 208 C1 | 9/2001 |
| EP | 0 161 686 A2 | 11/1985 |
| EP | 0 366 950 A1 | 5/1990 |
| EP | 0 560 368 A2 | 9/1993 |
| EP | 1 295 617 A1 | 3/2003 |
| EP | 1 457 218 A1 | 9/2004 |
| WO | WO 96/40320 A1 | 12/1996 |
| WO | WO 01/07136 A1 | 2/2001 |
| WO | WO 02/098491 A1 | 12/2002 |

* cited by examiner

*Primary Examiner* — John Kim
(74) *Attorney, Agent, or Firm* — Pearne & Gordon LLP

(57) ABSTRACT

A patient end of a venous blood line (26) is connected to a discharge of a dialysis liquid preparation circuit by means of an auxiliary connector (23), and the patient end of an arterial blood line (25) is connected to a service line (32) located at the top of a venous expansion chamber (31). The filling and/or rinsing liquid is removed from the preparation circuit by backfiltering through a membrane (5) of a high-flux dialysis filter (2). The invention enables a blood circuit to be primed simply and rapidly.

15 Claims, 6 Drawing Sheets

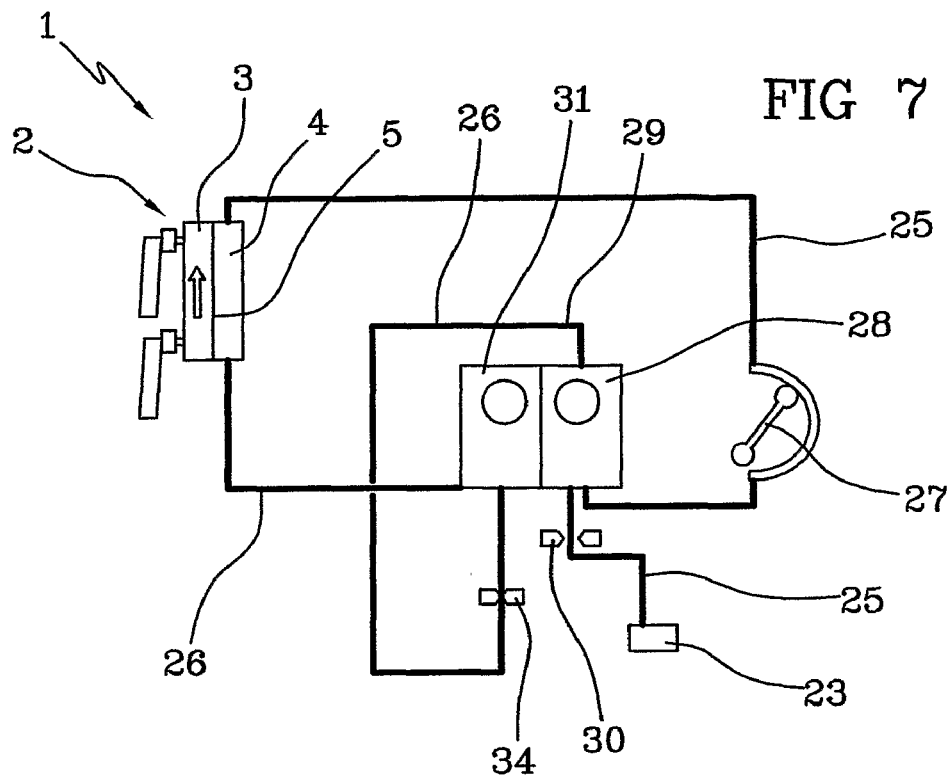
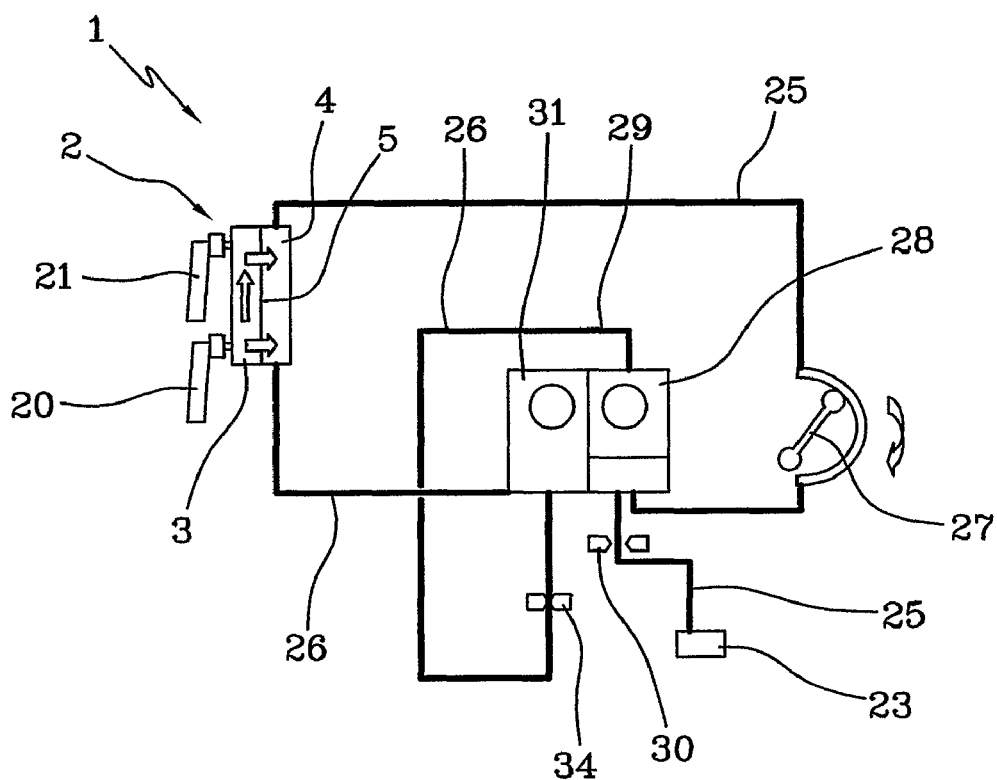

PROCESS AND AN APPARATUS FOR FILLING AND/OR RINSING AN EXTRACORPOREAL BLOOD CIRCUIT

BACKGROUND OF THE INVENTION

The invention relates to a process and an apparatus for filling and/or rinsing an extracorporeal blood circuit.

Specifically, though not exclusively, the invention can be usefully applied for priming an extracorporeal circuit in a dialysis apparatus.

As is well-known, before performing a dialysis treatment, the extracorporeal blood circuit of the dialysis apparatus has to be filled with an isotonic fluid, normally a sodium chloride solution with a concentration of 155 mmol/l. This procedure, known as "priming", has the aim of rinsing the circuit and removing the air and any particles and sterilising agents which might still be in the circuit.

With the aim of eliminating all of the air and filling with liquid both the blood side and the dialysis side of the dialyser, the prior art comprises a priming process in which the dialyser is first rinsed on one side, for example the dialysis side, from the bottom to the top; then it is upturned and rinsed on the other side.

Also known are various procedures which avoid the need to upturn the dialyser. One of these, used in the Seratron machine (Seratronics, Walnut Creek, Calif., USA) includes inverting the flow on the blood side of the dialyser. Other procedures include inverting the flow on the dialysis side by means of valves or pumps (see for example U.S. Pat. No. 4,324,662 and EP 0 366 950). EP 0 161 686 includes evacuating the air from the blood side by means of an aspiration unit in order to enable a following filling-up with the physiological solution. Finally, various methods are also known which include filling the blood side by backfiltering, i.e. forcing the liquid to transfer from the dialysis side to the blood side across the dialyser membrane.

Normally known priming procedures include, after the stage of complete filing of the extracorporeal circuit with the isotonic solution, a rinsing stage so that the isotonic solution in circulation is free of particles and sterilising agent. Finally the extracorporeal circuit is connected up to the patient: to do this the arterial line of the circuit is usually connected to the patient and the blood is made to enter the circuit by the blood pump, while the isotonic solution is sent to a discharge through the outlet of the venous line. When the blood arrives in proximity of the outlet of the venous line the blood pump is stopped to enable the venous line to be connected up to the patient. Alternatively the venous line is connected to the patient before activating the blood pump, so that the isotonic solution is infused into the patient and not discharged externally.

The process for filling the extracorporeal blood circuit according to the present invention is of the backfiltering type. There follow some descriptions of some known processes for filling via backfiltering.

DE 34 42 744 describes a process for re-use of a dialyser, according to which the used dialyser is first cleaned and disinfected, and then rinsed and tested. During the cleaning and disinfecting stage the dialyser is connected to the dialysis liquid circuit and to the extracorporeal blood circuit, as it is during a treatment, while the patient connection to the arterial line is connected to the fresh dialysis supply liquid and the patient connection line to the venous line is connected to the used dialysis liquid discharge line. A cleaning and disinfecting liquid is circulated along the fresh dialysis liquid supply line, then along the arterial line and then the venous line, and is finally discharged through the used dialysis liquid discharge line. During this stage, among other things, at least a small part of the cleaning and disinfecting liquid is forced to pass from the dialysis side of the dialyser to the blood side in backfilter through the membrane, in order to detach the layer of proteins that adheres to the blood side surface of the membrane. During the following rinsing stage, the patient connection to the arterial line is connected, by means of an adapter, to the patient connection to the venous line, so as to create a closed circuit; then the blood pump is set to operate continuously while the closed circuit is cyclically and repeatedly filled and emptied with water coming from the dialysis circuit, which is forced to pass through the dialyser membrane, alternatingly backfiltering and ultrafiltering. Then the water inside the blood circuit is dialyzed by the dialysis liquid flowing through the dialysis circuit.

A drawback of the process of DE 34 42 744 is that the rinsing stage is long, as an efficient rinse requires a passage of the liquid in both directions alternatingly for a considerable number of cycles. The rinse times are further lengthened because the passage of liquid through the membrane, both during the filling stage and the discharge stage, is by necessity relatively slow.

A further drawback of the process of DE 34 42 744 is that the rinsing action does not entirely purge the extracorporeal circuit of any particles remaining after the cleaning and disinfection stage which are bigger than the pores of the membrane.

A further drawback of the process of DE 34 42 744 is that the extracorporeal blood circuit is provided with a breather device that is relatively complex and expensive.

U.S. Pat. No. 5,259,961 describes some processes for rinsing, degassing and filling an extracorporeal blood circuit used in a dialysis apparatus.

In a first process described in U.S. Pat. No. 5,259,961, the dialyser is connected to the dialysis liquid circuit of the machine, as happens during a treatment; an end of the arterial line is connected, by means of an adapter, to the dialyser venous connection; the pump segment of the arterial line is connected to the blood pump; the other end of the arterial line is connected to an end of the venous line, while the other end of the venous line is connected, by means of a three-way valve, to the drainage line of the dialysis liquid discharging from the dialyser. The dialysis liquid prepared by the machine for dialysis is conveyed, by the blood pump, through the dialyser membrane (where it is filtered) into the arterial line and then to the venous line, then to return into the dialysis liquid circuit through the three-way valve.

This first process of U.S. Pat. No. 5,259,961 has, however, the drawback that various operations have to be performed after the circuit priming and before the dialysis treatment; the arterial line, for example, has to be detached from the venous connection of the dialyser and engaged to the arterial connection; further, the venous line has to be detached from the arterial line and engaged to the venous connection. This means not only more laborious activity for the operator, but also leads to a risk of circuit contamination.

In a second process described in U.S. Pat. No. 5,259,961, the arterial line and the venous line are connected, at an end thereof, to the respective arterial and venous connections of the dialyser, and at the opposite ends thereof to a valve arranged on the dialysis liquid circuit drainage line. The valve is commanded so as to prevent, totally or partially, the outflow from the dialysis chamber of the dialyser and to permit the drainage of the liquid from the arterial and venous lines towards the machine discharge. The dialysis liquid coming from the dialysis machine is forced, by the supply pump in the dialysis liquid circuit, to pass through the dialyser membrane into the venous and arterial lines, to perform the rinse and filling thereof, then to be discharged through the drainage line of the dialysis liquid circuit. Alternatively, the liquid used can be discharged into a further recipient.

A drawback of the second process of U.S. Pat. No. 5,259, 961 derives from the presence of two ends (one on the venous line and the other on the arterial line) communicating with a discharge, with a consequently greater risk of contamination of the circuit with respect to the first process of U.S. Pat. No. 5,259,961, in which only one end (the venous end) communicates with the discharge.

EP 0 560 368 describes various processes for rinsing and filling an extracorporeal circuit of a dialysis machine, according to which the arterial line and the venous line are connected to the dialyser in the same way as during dialysis treatment, the pump segment of the arterial line is connected to the blood pump and the patient connection of the arterial line is connected to the patient connection of the venous line, in order to create a closed circuit. During the rinsing and filling of the extracorporeal circuit, the blood pump is activated to function in a reverse direction to normal functioning direction during dialysis treatment, thus generating a depression which aspirates the dialysis liquid, forcing it to pass through the dialyser membrane to enter the closed-circuit extracorporeal circuit. Furthermore, a service line connected to the upper part of the venous expansion chamber is connected to outside of the extracorporeal circuit in order to enable air to be expelled, together with excess liquid present in the circuit.

In a first process of EP 0 560 368, a valve closes the venous line between the venous expansion chamber and the dialyser, while the service line is connected to a collection container or to the machine dialysis liquid circuit. To intensify and complete the rinse of the whole closed circuit the valve between the venous chamber and the dialyser is repeatedly opened and at the same time another valve closes the service line; if required, the blood pump direction can be inverted in order to operate in the direction of normal use during treatment.

This first process of EP 0 560 368, however, has the drawback of considerable complication, due to the use of two closure valves (one on the venous line between the expansion chamber and the dialyser and the other on the venous service line connected to the discharge) which are added to the closure valve normally present on the venous line between the expansion chamber and the patient connection.

In a second process of EP 0 560 368, the valve for closing the venous line between the venous expansion chamber and the dialyser is no longer necessary, while the service line is placed in communication with an aspiration device, such as for example the degassing system of the dialysis machine, so that the rinsing liquid can circulate along the whole circuit formed by the extracorporeal circuit.

The second process of EP 0 560 368 is however affected by a considerable complication due to the use of as aspiration device which, even if present on the machine for other reasons, has to be adapted and commanded to perform a further function.

In a third process of EP 0 560 368, the service line is connected to the dialysis liquid supply line and is operatively associated to a reversible pump, i.e. a pump that can circulate liquid in both directions. The service line also exhibits a block valve, arranged between the reversible pump and the venous expansion chamber, and an elastic bag of about 20-50 ml volume, arranged between the reversible pump and the block valve to form a variable-volume chamber. During the rinsing and filling stages, the reversible pump operates as an aspiration device for expelling the excess air and the liquid. During the dialysis treatment, in which the block valve is always closed, the reversible pump periodically sends the liquid contained in the elastic bag to the dialysis side of the dialyser, to wash out the membrane by backfiltering, to detach the layer of proteins that deposits on the blood side of the membrane. The volume of cleaning liquid in the elastic bag is restored by inverting the operating direction of the reversible pump.

This third process too of EP 0 560 368 requires the use of a rather complex apparatus.

U.S. Pat. No. 6,132,616 describes a rinsing and filling process of an extracorporeal blood circuit in a dialysis apparatus, in which the rinsing liquid is forced to pass through the dialyser membrane from the dialysis side to the blood side. The arterial line and the venous line are connected to each other in such a way as to create a closed circuit. A three-way shunt valve, predisposed on the venous line in proximity of the patient connection end, enables drainage of the rinsing liquid from the blood circuit through a branch conduit communicating with one way of the shunt valve, on one side, and with a dialysis liquid preparation circuit on the other side. This stage lasts for a predetermined time, after which the blood pump recirculates, in a closed circuit, the rinsing liquid left in the circuit, while a dialysis liquid circulates in the dialysis compartment of the dialyser, until the ionic concentration of the liquid in the extracorporeal circuit reaches that of the dialysis liquid by means of diffusion through the membrane.

The process described in U.S. Pat. No. 6,132,616 is somewhat complicated, however, due to the presence of both a special intermediate point of connection of the extracorporeal circuit from which the branch conduit branches off, and because of a special three-way shunt valve predisposed in the above-mentioned intermediate point of connection in order to enable drainage of the extracorporeal circuit through the branch conduit.

U.S. Pat. No. 6,277,272 describes a process for priming and cleaning the extracorporeal blood circuit in a dialysis apparatus having a fluid balancing device, of a type comprising volumetric chambers. A pressurisation line is arranged in parallel to the fresh dialysis fluid supply line in order to bypass the volumetric chamber of the fresh dialysis liquid. According to the process of U.S. Pat. No. 6,277,272 the fresh dialysis liquid is forced to pass through the dialyser membrane in the extracorporeal circuit arranged on the pressurisation line. In a first stage the blood pump rotates in the inverse direction with respect to the normal blood circulation direction and the venous line closure valve is active, so that the dialysis fluid performs the priming and cleansing of the arterial line and then is discharged through the line itself. In a second stage, the occlusive blood pump is stopped and the valve on the venous line opened, while the pressurisation pump pushes the dialysis liquid through the membrane and thus along the venous line, towards the patient connection which functions as a discharge end.

A drawback of the process of U.S. Pat. No. 6,277,272 is its complexity, due to the use of a pressurisation line and pump. A further drawback is the presence of two connections with the discharge, which leads to a greater risk of contamination of the extracorporeal circuit.

EP 1457218 describes an automatic priming system of an extracorporeal circuit, by backfiltering through the dialyser membrane, comprising a reversible blood pump, an evacuation line connected to the top of the venous expansion chamber to eliminate excess liquid, a first clamp on the evacuation line, a second clamp on the venous line between the expansion chamber and the dialyser, a first pump on the supply line of the freshly dialyzed liquid to the dialyser, a bypass line with two ends connected to the drainage line to bypass the drainage pump, and an adjustment pump for the backfiltering rate arranged on the bypass line. EP 1457218 describes various priming processes of the extracorporeal circuit, according to which: the arterial line and the venous line are connected to the dialyser, as during the treatment, and are connected up to one another at the patient connections; the backfilter flow rate through the membrane of the dialyser is regulated by means of the regulation pump; and the flow rate of the excess liquid through the evacuation line is regulated in combination by the regulation pump and the blood pump, inversely activated.

EP 1457218 has however the drawback of having a certain constructive complexity, due to the predisposition of the bypass line and the regulation pump, together with the fact that at the end of the priming operation the venous expansion chamber liquid level has to be adjusted.

U.S. Pat. No. 5,863,421 describes a machine for dialysis which uses an automatic priming process of the dialyser membrane, in which a control unit activates the blood pump, the dialyzed liquid pump and two check valves (clamps), one on the arterial line and the other on the venous line, so as to force a priming liquid from the dialysis side to the blood side of the dialyser through the membrane, in synchrony with the induction of a multiplicity of small and repeated pressure pulses in the extracorporeal circuit, with the aim of detaching the air bubbles from the blood side of the membrane.

DE 10011208 describes a process for filling and rinsing an extracorporeal circuit in which a sterile liquid is supplied along the circuit up to an empty re-infusion container through a secondary line which branches from the arterial line. The sterile liquid, before entering the extracorporeal circuit, is filtered through the membrane of the dialyser or a sterile filter.

U.S. Pat. No. 6,331,252 is a process for priming the blood side of a dialyser having the dialysis side connected to a preparation circuit of the dialysis liquid. A measured flow of dialysis liquid is conveyed to a first pump, then to a first flow meter and then to the inlet of the dialysis side of the dialyser. A part of the flow is forced to pass through the membrane of the dialyser in order to prime the blood side, while the remaining part is conveyed to the outlet of the dialysis side of the dialyser and then to a second flow meter and to a second pump. The two pumps are commanded by flow rate signals supplied by the flowmeters so that the flow rate on the outlet of the dialysis side is lower than the flow rate at the inlet.

WO 02/098491 describes a process for filling and washing a dialyser, the dialysis side of which is filled with a physiological solution, a part of which is forced to pass through the membrane of the dialyser into the blood side and then into the extracorporeal circuit. The patient connections of the arterial and venous lines are connected to one another so as to form a closed circuit. The blood pump is of the reversible type, able to circulate the liquid in both directions. The arterial expansion chamber is connected to the outside ambient. The physiological solution which fills the extracorporeal circuit is drained through the discharge connectable to the patient connection of the arterial line.

SUMMARY OF THE INVENTION

An aim of the present invention is to provide a filling and/or rinsing process of an extracorporeal blood circuit which can be performed rapidly and simply by an operator.

A further aim of the invention is to realise an apparatus which is simple and economical and able to actuate the above-mentioned process.

A further aim of the present invention is to provide a filling and/or rinsing process and apparatus which overcomes the above-described drawbacks in the prior art.

An advantage of the invention is that it can provide a priming system, of a backfiltering type, which does not require a bag for containing the priming solution.

A further advantage is to provide a rapid and effective system for filling, emptying of air and rinsing an extracorporeal circuit. Particularly advantageous are the high level of automation of the priming process, and the fact that the discharge of excess liquid can be done through a rapid outflow discharge and not, for example, through a semipermeable membrane.

A still further advantage is that during the priming process the arterial line and the venous line can be connected to the blood treatment device (dialyzer), as during treatment, with a consequent simplification of the subsequent readying operations of the treatment apparatus and the reduction of contamination risks.

During the priming process of the extracorporeal circuit it is advantageous that only one output end of the circuit can be connected to a discharge, thus reducing the risk of contamination.

A further advantage is the possibility of setting the level of liquid simply and immediately both in the venous expansion chamber (also known as the drip chamber) and the arterial expansion chamber during the priming process.

The filling system is further especially advantageous by virtue of its constructional simplicity, in which the discharge of the excess liquid can be effected without using either specific intermediate branch points along the extracorporeal circuit or special three-way valves connected to the circuit on one side and the discharge on another side, or aspiration device for forcing the excess liquid to outlet from the circuit. It is true that the preferred embodiments of the invention described herein comprise an aspiration device for facilitating the evacuation of the air and the excess liquid from the extracorporeal circuit towards the preparation circuit of the treatment liquid; however, this is not strictly necessary for the effectiveness of the process, which can include, for example, the discharge of the air and liquid in excess from the extracorporeal circuit into an external container (open bath or closed variable-volume bag) which can be in this case neither connected to a preparation circuit of the treatment liquid nor connected to any aspiration device at all.

A further advantage is that the preparation circuit of the dialysis liquid, from which originates the liquid used for the extracorporeal circuit priming process, does not require modifications and adapting with respect to the existing preparation circuits; for example, a pressurisation circuit in parallel to the normal supply circuit is not necessary, as in U.S. Pat. No. 6,277,272.

These aims and advantages and more besides, which will better emerge during the description that follows, are attained by a process and a device for filling according to one or more of the appended claims.

Further characteristics and advantages of the present invention will better emerge from the detailed description that follows, of at least an embodiment of the invention which is illustrated purely by way of non-limiting example in the accompanying figures of the drawings.

BRIEF DESCRIPTION OF THE DRAWINGS

The description will be made with reference to the accompanying figures of the drawings, included by way of non-limiting example, and in which.

Figure 1:
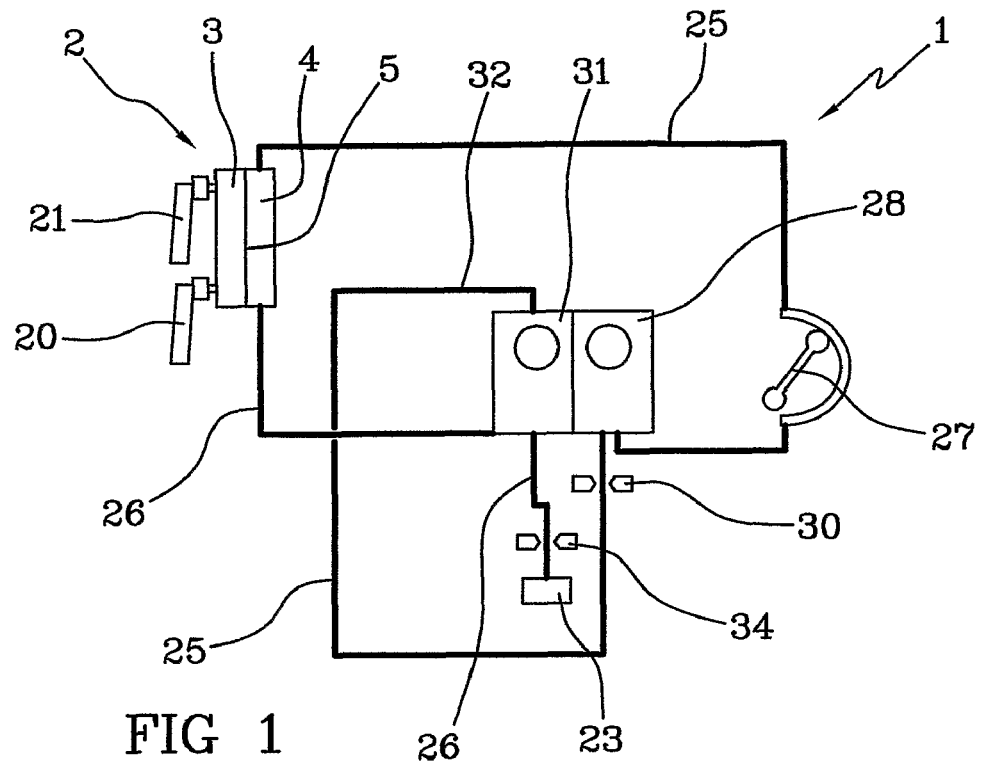
FIG. 1 is a first embodiment of an apparatus for priming an extracorporeal circuit.
Figure 6:
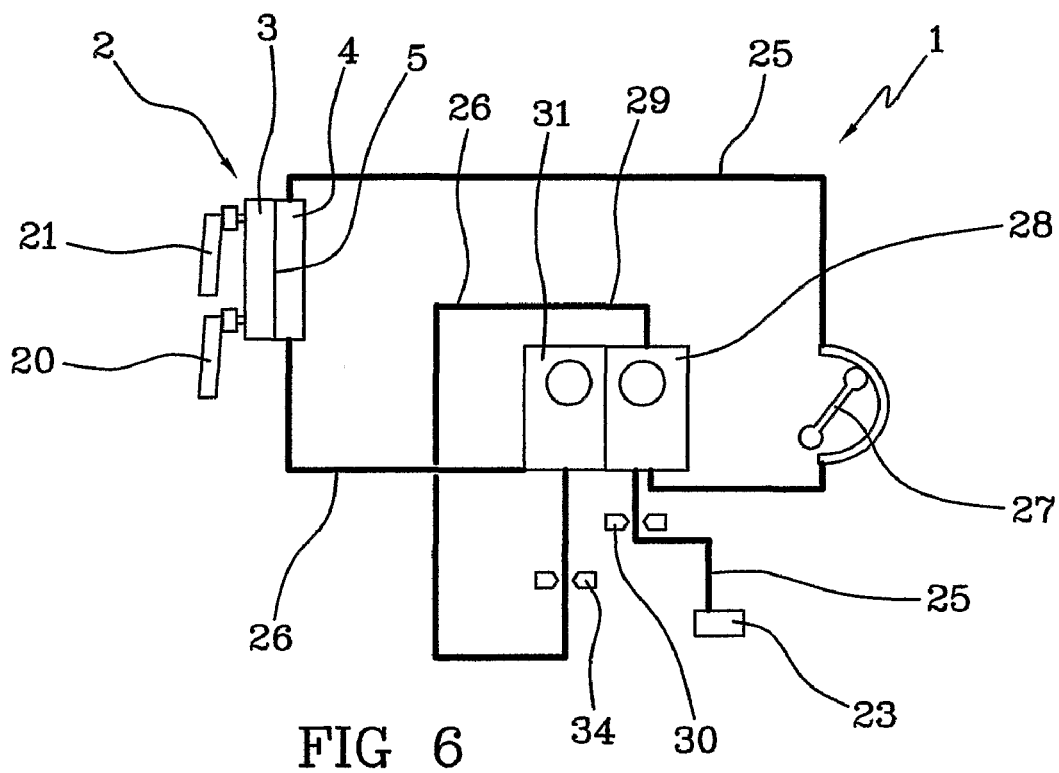
Figure 11:
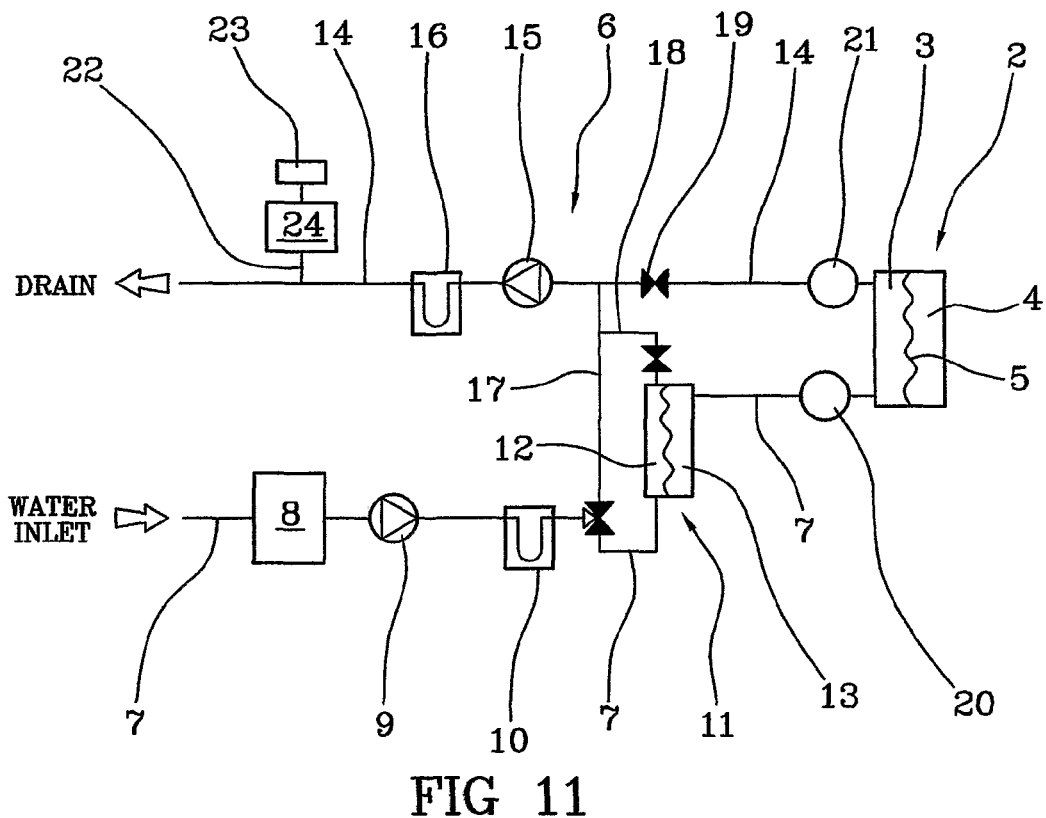
Figure 12:
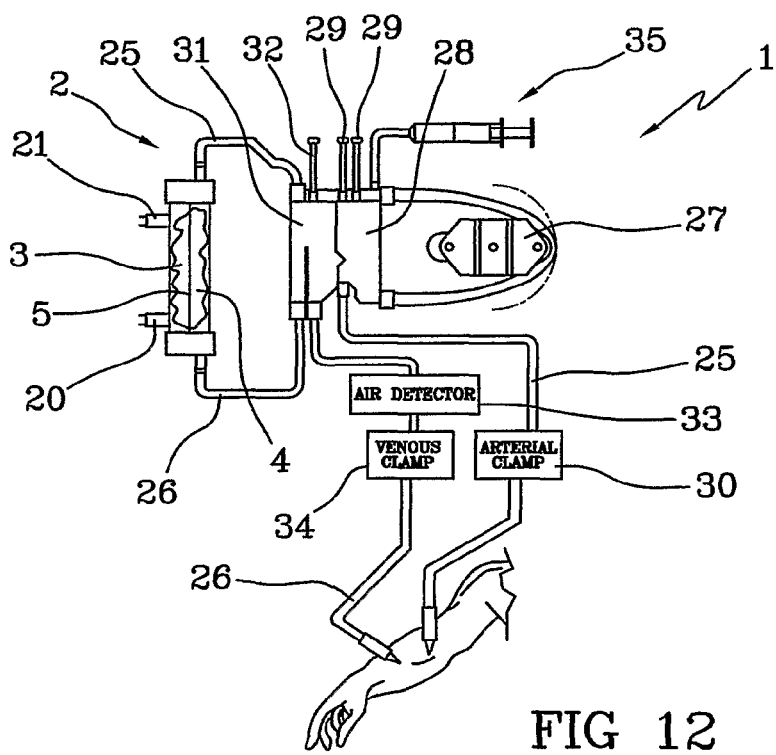

FIGS. from 2 to 5 show various stages of filling actuated by the apparatus of FIG. 1;

FIG. 6 is a second embodiment of an apparatus for filling an extracorporeal circuit;

FIGS. from 7 to 10 show various stages of the filling process of the apparatus of claim 6;

FIG. 11 shows a preparation circuit of a dialysis liquid used in both apparatuses of FIGS. 1 and 6;

FIG. 12 is a detailed illustration of the extracorporeal circuit of FIGS. 1 and 6.

DETAILED DESCRIPTION

With reference to FIGS. 1, 11 and 12, 1 denotes in its entirety an extracorporeal blood circuit, in particular an extracorporeal blood circuit applicable in an apparatus for extracorporeal blood treatment, comprising a blood treatment device 2 having a fluid chamber 3 and a blood chamber 4 separated by a semipermeable membrane 5. The treatment device is, in the specific case, a high-flux dialyser.

The apparatus for extracorporeal blood treatment can be predisposed to effect, for example, one or more of the following extracorporeal treatments: hemodialysis, hemofiltration, hemodiafiltration, pure ultrafiltration.

The treatment apparatus can be, in particular, predisposed for in-line preparation of a treatment liquid (dialysis liquid and/or substitution liquid). The treatment apparatus comprises in particular a treatment liquid preparation circuit 6 (see FIG. 11) provided with a fresh liquid supply line 7 connected to an inlet of the fluid chamber 3. The supply line 7 comprises an inlet for water, a treatment liquid preparation device 8 (of known type) which receive the water coming from the water inlet, a first liquid circulation pump 9, a first flowmeter 10 for determining the liquid flow rate, a filter 11 having a first chamber 12 and a second chamber 13 separated by a semipermeable membrane. The first chamber 12 of the filter has an inlet which receives the treatment liquid from the preparation device 8. The second chamber 13 of the filter has an outlet which is connected to the inlet of the fluid chamber 3 of the treatment device. The preparation circuit 6 further comprises a drainage line of the used treatment liquid 14 which connects an outlet of the fluid chamber 3 with a discharge. The drainage line 14 comprises a second liquid circulation pump 15 and a second flowmeter 16. The preparation circuit 6 comprises a first bypass line 17 which connects the supply line 7 (at a point downstream of the first flowmeter 10 and upstream of the filter 11) with the drainage line 14 (at a point upstream of the second flowmeter 16). The preparation circuit 6 comprises a second bypass line 18 which connects an outlet of the first chamber 12 of the filter with the drainage line 14 (at a point upstream of the second flowmeter 16). The first and second bypass lines 17 and 18 are provided with respective bypass valves (see FIG. 11). A check valve 19 is predisposed on the drainage line 14 upstream of the bypass lines 20 and 21 denote two connections for removable connection of the fluid chamber 3 of the treatment device with the fresh liquid supply line 7 and, respectively, with the used liquid drainage line 14. In the preferred embodiment the treatment device 2 is conformed and arranged in such a way that in the priming configuration and in the treatment configuration alike, the inlet connection 20 is arranged inferiorly of the outlet connection 21.

The treatment apparatus comprises an auxiliary line 22 extended between the drainage line 14 (downstream of the second flowmeter 16) and an auxiliary connector 23 which serves to removably connect the fluid to an external element connected to the extracorporeal circuit 1 (as will be explained in more detail herein below). An aspiration device 24 (for example a membrane pump) is predisposed on the auxiliary line 22 for aspirating a fluid from the extracorporeal circuit 1.

The extracorporeal blood circuit 1 has a arterial blood line 25 and a venous blood line 26, each of which is provided with a patient end and a device end (see FIG. 12). The extracorporeal blood circuit 1 (of known type) in FIG. 12 is illustrated in the treatment configuration. The arterial line 25 comprises a pump segment connected to a blood pump 27 which is reversible (i.e. can operate in both rotation directions to enable circulation of liquid in the extracorporeal circuit in both circulation directions). The arterial line 25 further comprises an arterial expansion chamber 28 having a blood inlet and a blood outlet arranged on the lower zone of the chamber (the blood inlet is higher than the blood outlet) and one or more service lines 29 communicating with the upper part of the chamber 28. The extracorporeal apparatus 1 is provided with an arterial clamp 30 operative on the arterial line 25 between the blood pump 27 and the patient end. The venous line 26 comprises a venous expansion chamber 31 having a blood inlet and a blood outlet arranged on the lower zone of the chamber (the blood inlet being higher than the blood outlet) and at least a service line 32 communicating with the upper part of the chamber 31. The extracorporeal apparatus is provided with an air sensor 33 and a venous clamp 34 operating on the venous line 26 between the expansion chamber 31 and the patient end. The arterial and venous chambers 28 and 31 are incorporated in a cassette of known type (a cartridge which is marketed by Hospal®). In FIG. 12, 35 denotes an infusion device operating on the arterial line 25, for example upstream of the blood pump 27, and used, in particular, for infusion of an anticoagulant.

The extracorporeal circuit 1 is represented in FIGS. 1 and 12 during the priming process and, respectively, during the extracorporeal treatment. During the priming (FIG. 1) the device ends of the blood lines are connected to the blood chamber 4, as during treatment, while the patient end of the arterial line 25 is connected to an intermediate zone of the venous line 26 and the patient end of the venous line 26 is connected to the discharge of the preparation circuit 6 via the auxiliary connector 23. The extracorporeal circuit is conformed and arranged in such a way that, in the priming configuration, the device connection of the arterial line 25 is arranged above the device end of the venous line 26.

The treatment apparatus comprises a control unit connected to the actuators (blood pump 27, first circulation pump or supply pump 9, second circulation pump or drainage pump 15, arterial and venous clamps 30 and 34, first and second bypass valves, check valve 19, actuator or actuators of the aspiration device 24, treatment liquid preparation device 8) and the sensors (first and second flowmeters 9 and 16, air sensor 33, sensor or sensors of the treatment liquid preparation device 8, usual pressure sensors on the blood circuit 1 and the treatment liquid preparation circuit 6) of the treatment apparatus. The control unit is also connected to other actuators and sensors, of known type and not illustrated, normally used in a dialysis apparatus. The control unit is programmed to carry out a process for filling the extracorporeal circuit comprising the stages described herein below.

The cassette which incorporates the expansion chambers 28 and 31 is inserted, in a known way, on a front panel of the treatment apparatus. The connection on the patient end of the venous line 26 is connected to the auxiliary connector 23 communicating with the treatment liquid preparation circuit 6. The auxiliary connector 23 can comprise, for example, a counter-connector of the luer type (female) couplable to the male luer connector normally present at the patient end of a blood line. The arterial line 25 is coupled to the arterial clamp 30. The connection on the patient end of the arterial line 25 is connected to the connection of the service line 32 of the venous expansion chamber 31. This connection of the service line 32 can comprise, for example, a female luer counter-connector couplable to the male luer connector normally present at the patient end of a blood line. The venous line 26 is coupled to the venous clamp 34 and the air sensor 33. The connections on the device ends of the arterial and venous lines 25 and 26 are connected to the respective connections of the blood chamber 4, as during treatment. The connections 20 and 21 of the treatment liquid preparation circuit 6 are connected to the fluid chamber 3 of the treatment device 2. Finally the user selects a specific button on the screen of the user interface of the treatment apparatus for activating the automatic priming process. The control unit consents to the start of the priming process only on the condition that the treatment liquid has determined temperature conditions and electrical conductivity, as measured by the treatment liquid preparation device 8 sensors.

Figure 2:
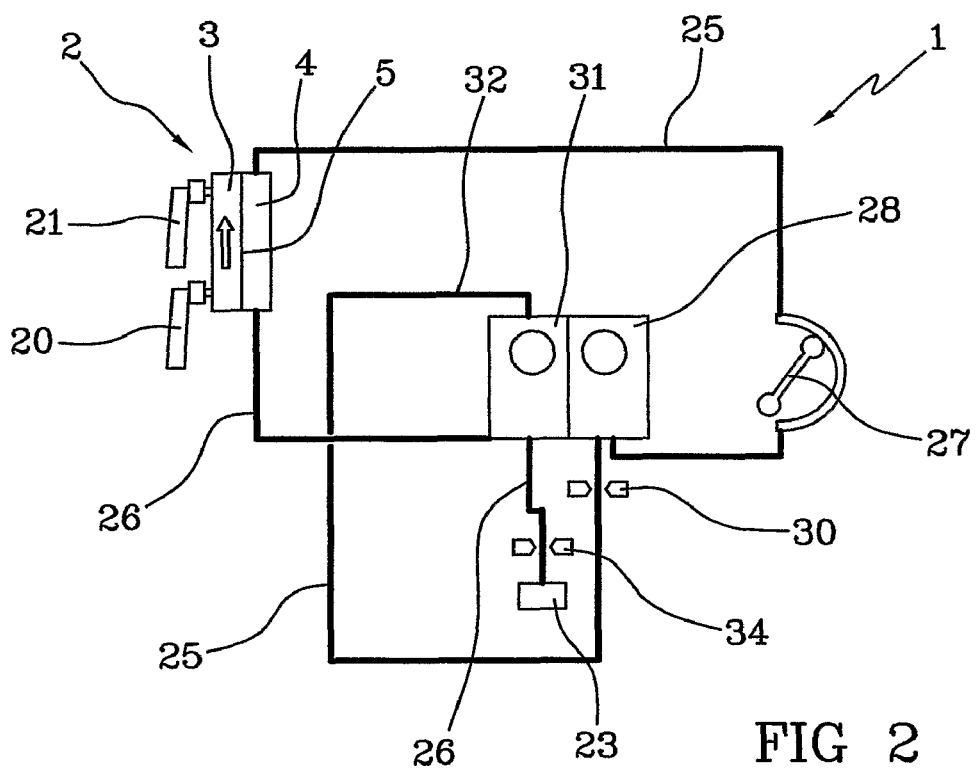

In a subsequent stage (FIG. 2) of air removal from the fluid chamber 3 of the treatment device 2, the treatment liquid is conveyed along the supply line 7 up to the fluid chamber 3, proceeding in an upwards direction, and from which it is sent to the discharge along the drainage line 14. The supply and drainage pumps 9 and 15 are controlled in such a way that the pressure in the circuit 6 is at a predetermined level: in particular the pressure on the drainage line 14 in proximity of the outlet of the fluid chamber 3 is kept at a predetermined value below zero (for example −100 mmHg). During this stage the air contained in the fluid chamber 3 is expelled through the fluid port of the chamber 3 located superiorly and is thus eliminated through the line 14 and the discharge. The bypass lines 17 and 18 are closed, the check valve 19 is open, the venous clamp 34 is open, the arterial clamp 30 is open, the blood pump 27 and the aspiration device 24 are inactive. This stage is concluded when an air sensor (not illustrated) arranged on the drainage line 14 stops signalling the presence of air, or after a predetermined period of time.

In a subsequent stage (FIG. 3), in which the air present in the blood chamber 4 of the treatment device 2 and the arterial line 25 is removed, the treatment liquid is used as a filling liquid which is introduced into the blood circuit 1 through the membrane 5 of the treatment device 2, passing from the fluid chamber 3 to the blood chamber 4 and from here along at least a part of the extracorporeal circuit 1 up to the discharge, through the auxiliary connector 23. During this stage the supply and drainage pumps 9 and 15 are controlled so that the pressure in the fluid chamber 3 (measured upstream of the inlet and/or downstream of the fluid chamber outlet) is maintained at a predetermined level above zero (for example mean pressure=+100 mmHg) so as to determine a positive trans-membrane pressure from the fluid chamber 3 to the blood chamber 4. The venous clamp 34 remains open and the arterial clamp 30 also remains open. The aspiration device 24 is commanded to aspirate fluid from the blood circuit 1 towards the treatment liquid preparation circuit 6 at a predetermined flow rate (for example 120 ml/min), while the blood pump 27 is commanded to convey fluid in a circulation direction which goes from the blood chamber 4 to the arterial expansion chamber 28 and from here to the arterial patient end, then to the venous expansion chamber 31 and finally to the discharge. The blood pump 27 rotates in the direction indicated by an arrow in FIG. 3, i.e. in the opposite direction to the treatment direction. The blood pump 27 is commanded to convey a slightly lower flow than the flow of the aspiration device 24 (for example 100 ml/min). This stage terminates when the air sensor 34 on the venous line 26 stops signalling the presence of air, or when the liquid level in the arterial chamber 28 has reached a maximum predetermined threshold, or after a predetermined time period, or when the total volume displaced by the blood pump 27 has reached a predetermined value (for example 200 ml). During this stage the filling liquid is circulated along a path which comprises, in order, the membrane 5, the blood chamber 4, the arterial line 25 up to when it reaches an intermediate zone of the venous line 26 (the venous chamber 31), and a tract of the venous line 26 between the intermediate zone and the discharge. During this stage the air contained in the upper part of the blood chamber 4, in the arterial line 25, in the venous expansion chamber 31, and in the terminal part of the venous line 26 is evacuated through the auxiliary connector 23 of the patient end of the venous line 26. The expelled air is substituted by the treatment liquid pushed through the membrane 5 by the positive trans-membrane pressure going from the fluid chamber 3 to the blood chamber 4. During this stage a liquid level in the arterial expansion chamber 28 is automatically created, which level is predefined by effect of the shape of the chamber itself, in which the fluid access port close to the blood pump 27 is at a lower level than the fluid access port which is further away from the blood pump 27. In the venous expansion chamber 31, no liquid level is created, by effect of the evacuating action of the aspiration device 24.

In a following stage (FIG. 4), in which the air in the blood chamber 4 and the venous line 26 is removed, the treatment liquid continues to be used as a filling liquid, being introduced into the blood circuit 1 through the membrane 5 of the treatment device 2, passing from the fluid chamber 3 to the blood chamber 4 and from there along at least a part of the extracorporeal circuit up to the discharge. As before, during this stage too the supply and drainage pumps 9 and 15 are controlled so that the pressure in the fluid chamber 3 is maintained at a predetermined value which is greater than zero (for example mean pressure of +100 mmHg) to generate a trans-membrane pressure which is sufficient to cause backfiltering. The venous clamp 34 and the arterial clamp 30 remain open. The aspiration device 24 continues as before to be controlled so as to aspirate fluid from the blood circuit 1 towards the treatment liquid preparation circuit 6 at a predetermined flow rate (for example 100 ml/min), or to maintain a predetermined pressure (for example −200 mmHg) in the extracorporeal circuit, while the blood pump 27 is commanded to sent fluid in an opposite circulation direction to the previous one (indicated by an arrow in FIG. 4) so as to convey a flow which is about equal to the flow of the aspiration device (for example 100 ml/min). This stage terminates when the air sensor 33 on the venous line 26 stops signalling the presence of air, or when the liquid level in the arterial chamber 28 has reached a minimum predetermined threshold level, or when after a predetermined time period, or when the total volume displaced by the blood pump 27 has reached a predetermined value (for example 250 ml). During this stage the filling liquid is recirculated, in a circulation direction opposite to the previous one, along a pathway that comprises, in succession, the arterial expansion chamber 28, the arterial pump segment, the blood chamber 4, the venous line 26 and the discharge. During this stage the air contained in the lower part of the blood chamber 4 and in the venous line 26 is discharged through the patient end of the venous line 26, and is replaced by the liquid coming from the treatment liquid preparation circuit 6. The liquid passes through the membrane 5 by effect of the thrust due to the positive trans-membrane pressure going from the fluid chamber 3 to the blood chamber 4. During this stage the blood pump 27 aspirates the air present in the upper part of the venous expansion chamber 31, conveying it along the arterial line 25 and towards the arterial expansion chamber 28, so that the liquid level in the arterial chamber 28 drops. Furthermore, the aspiration device 24 recalls the liquid coming from the blood chamber 4 through the venous line 26 towards the discharge, so that during this stage no liquid level is established in the venous expansion chamber 31.

Figure 3:
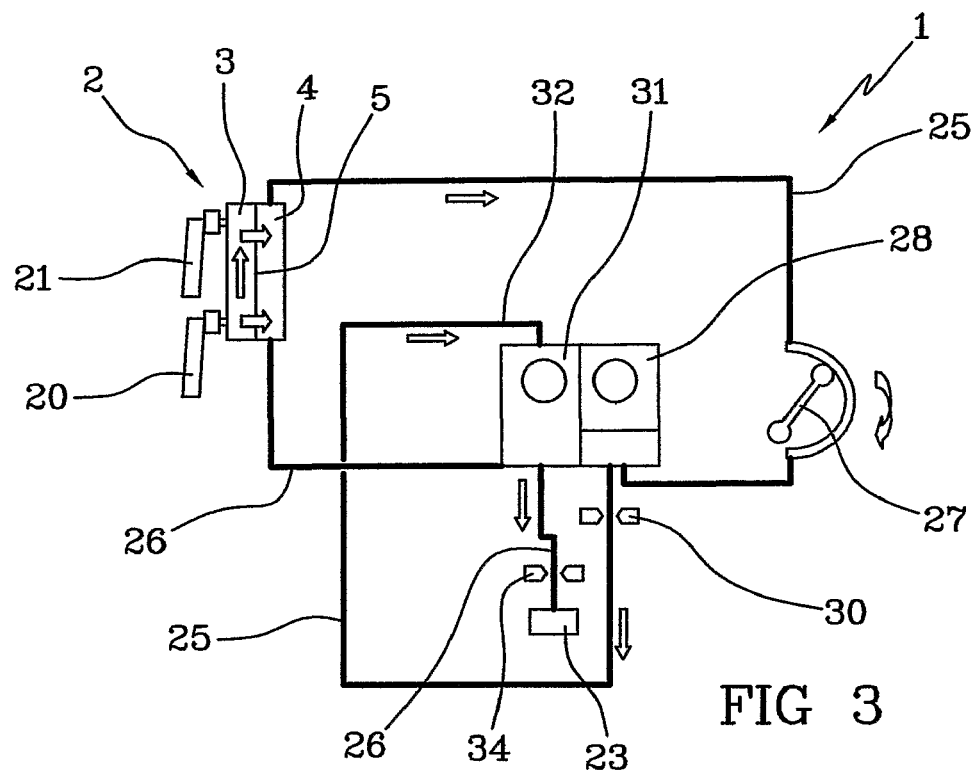
Figure 5:
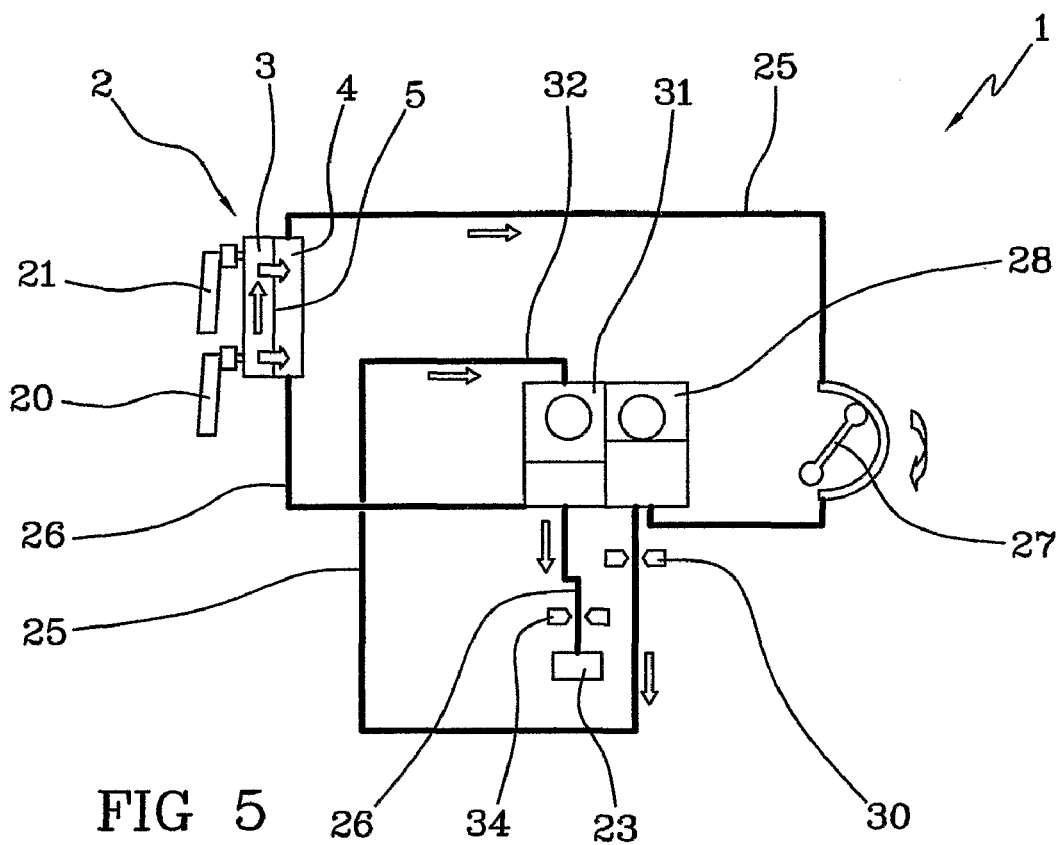

In a following stage (FIG. 5), in which the air present in the venous expansion chamber 31 is removed, the situation of FIG. 3 is restored; the treatment liquid passes through the membrane 5, the supply and drainage pumps 9 and 15 are commanded so that the pressure in the fluid chamber 3 is maintained at a predetermined value which is above zero (for example a mean pressure of +100 mmHg), the venous clamp 34 and the arterial clamp 30 stay open, the aspiration device 24 aspirates fluid at a predetermined flowrate (for example 240 ml/min), the blood pump 27 conveys fluid in the circulation direction from the blood chamber 4 to the arterial expansion chamber 28 and then to the arterial patient end, then to the venous expansion chamber 31 and finally to the discharge, at a slightly slower flow rate than that caused by the aspiration device 24 (for example 200 ml/min). This stage terminates when the air sensor 33 on the venous line 26 stops signalling the presence of air, or when the liquid level in the venous chamber 31 and/or the arterial chamber 28 has reached a maximum predetermined threshold level, or after a predetermined time period, or after the total volume displaced by the blood pump 27 has reached a predetermined value (for example 500 ml). During this stage the filling liquid is circulated along a pathway which comprises, in order, the membrane 5, the blood chamber 4, the arterial line 25 up to an intermediate zone (chamber 31) of the venous line 26, and a tract of the venous line 26 between the intermediate zone and the discharge. In this stage a part of the residual air contained in the venous expansion chamber 31 is discharged through the patient end of the venous line 26.

During this stage an automatic control of the process can be included, as described herein below. In a first sub-stage the aspiration device 24 is commanded to create a negative pressure in the blood chamber 4; the aspiration device 24 can be controlled, for example, by a signal indicating a flow rate so as to obtain a flow of a predefined value (for example a constant value of 150 ml/min); at the same time the blood pump 27 is commanded to generate a predefined flow which is less than the flow generated by the aspiration device 24 (for example 100 ml/min); in this situation the flow in the arterial line 25 is 100 ml/min, the flow in the tract of venous line 26 comprised between the blood chamber 4 and the venous expansion chamber 31 is 50 ml/min (directed towards the venous chamber 31), and the flow in the tract of venous line 26 comprised between the expansion chamber 31 and the patient end is 150 ml/min. In this first sub-stage the trans-membrane pressure increases by effect of the depression created by the aspiration device 24; the first sub-stage terminates automatically when the trans-membrane pressure reaches a predetermined threshold value (for example 200 mmHg), after which a second sub-stage automatically starts up, in which the aspiration device 24 is commanded to create a slower flow with respect to the flow of the first sub-stage (for example 110 ml/min), so that the flow in the tract, of venous line 26 comprised between the blood chamber 4 and the venous chamber 31 is slow (for example 10 ml/min): in this second sub-stage the flow can actually be zero or inverted with respect to the first sub-stage, if the aspiration device 24 flow becomes lower than the blood pump 27 flow. In this second sub-stage the trans-membrane pressure lowers, as the depression created by the aspiration device 24 diminishes. In this second sub-stage the trans-membrane pressure lowers, as the depression created in the aspiration device 24 drops. The second sub-stage terminates automatically when the trans-membrane pressure reaches a predetermined threshold value (for example 100 mmHg). These two sub-stages can be repeated cyclically and alternatedly several times.

Figure 4:
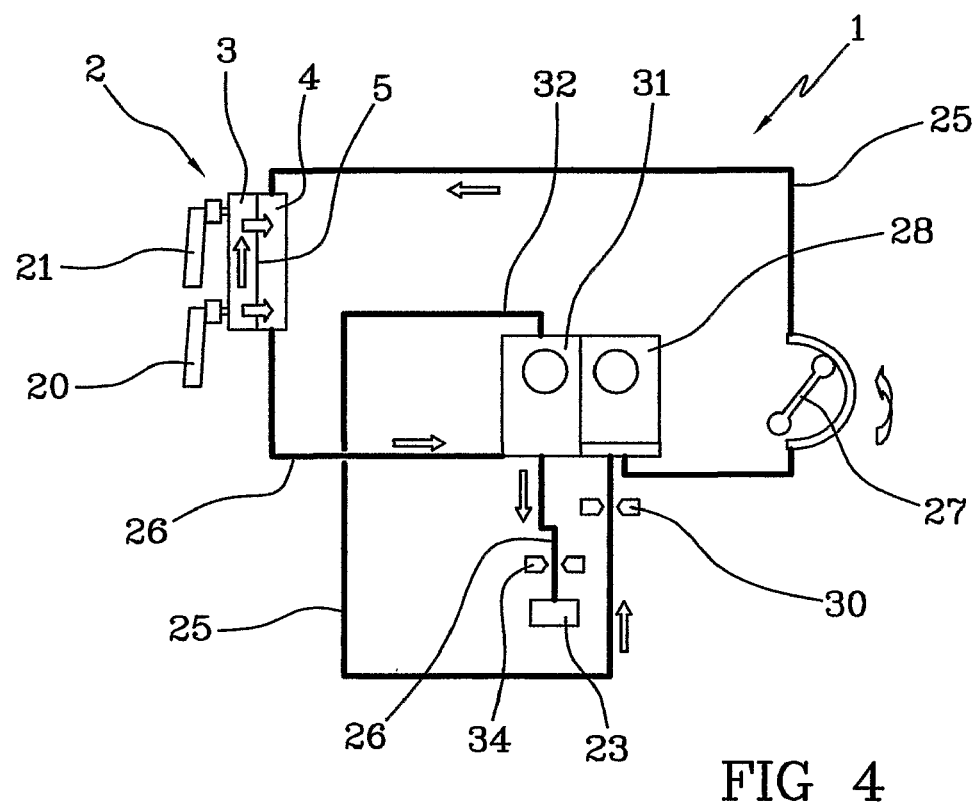

Further stages can be included in which the rotation direction of the blood pump 27 is reversed, i.e. alternating the described stage in relation to FIG. 3 with the stage of FIG. 4, until the air sensor 33 on the venous line 26 stops signalling the presence of air.

The control unit is programmed so that, if during the performing of one of the above-mentioned stages the transmembrane pressure (calculated in a known way from measured pressure values) exceeds a predefined value (for example 200 mmHg), the stage which is under way at that moment is automatically interrupted and the following stage is initiated.

Once the air contained in the extracorporeal blood circuit 1, including the blood chamber 4, the arterial line 25 and the venous line 26, has been sent to the discharge of the preparation circuit 6, the blood circuit 1 is filled with the filling liquid coming from the fluid chamber 3 of the treatment device 2. In particular it has emerged that the level of the filling liquid in the arterial expansion chamber 28 and the venous chamber 31 is defined simply and immediately.

When the priming process has terminated, the patient venous connection is already connected to a discharge (the discharge of the preparation circuit 6), i.e. in a configuration which is already suitable for connection to the patient's extracorporeal circuit, thus facilitating the readying of the treatment apparatus for the operator.

With reference to FIGS. from 6 to 10, a second embodiment of the invention is represented, which as before involves the use of the treatment liquid preparation circuit 6 of FIG. 11 and the extracorporeal circuit 1 of FIG. 12.

FIG. 6 shows the filling apparatus: the patient end of the arterial line 25 is connected to the auxiliary connector 23, while the patient end of the venous line 26 is connected to a service line 29 connected to the top of the arterial chamber 28. The connection to the service line 29 can use, for example, a counter-connector of the luer type (female) arranged at an end of the service line 29 and couplable to the male luer connector normally present at the patient end of a blood line. The arterial line 25 is connected to the blood pump 27. The device end of the arterial and venous lines 25 and 26 are connected to the treatment device 2 in the same treatment positions.

In a first stage of the filling process (FIG. 7), the fluid chamber 3 of the treatment device 2 is primed, by making the treatment liquid flow into the fluid chamber 3 from the bottom towards the top, so as to evacuate the air and fill the fluid chamber with the liquid The blood pump 27 is stationary. The venous clamp 34 is closed, while the arterial clamp 30 is open.

In a second stage (FIG. 8) a positive trans-membrane pressure is created from the fluid chamber 3 to the blood chamber 4. The treatment liquid passes through the membrane 5 and enters the extracorporeal circuit 1. The venous clamp 34 stays closed and the arterial clamp 30 stays open. The blood pump 27 is activated in an inverse direction (with respect to the direction used during treatment), so that the liquid entering the extracorporeal circuit 1 runs along the arterial line 25 from the blood chamber 4 up to the patient end, and then goes on to the discharge. During this stage the air in the upper part of the blood chamber 4 and the arterial line 25 is evacuated.

Figure 9:
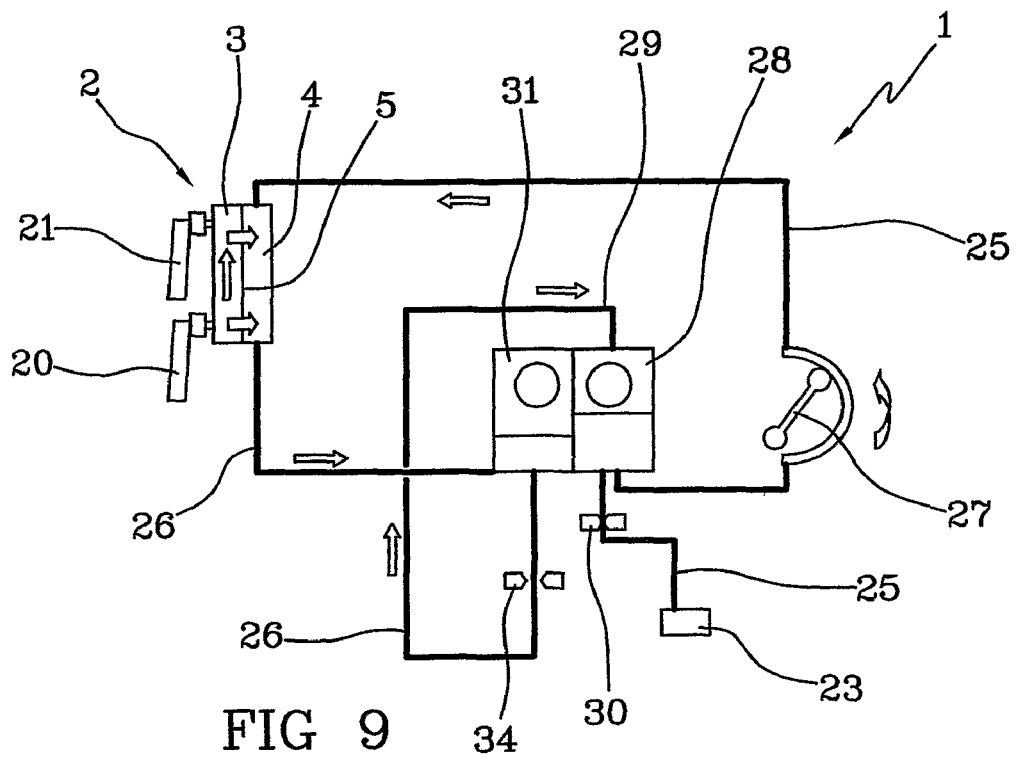

During a third stage (FIG. 9) a positive trans-membrane pressure is maintained to obtain backfiltering, while the blood pump 27 is activated inversely to its previous direction; the arterial clamp 30 is closed and the venous clamp 34 is opened. During this stage the liquid recirculates in a closed circuit and a liquid level is created in both the expansion chambers 28 and 31.

Figure 10:
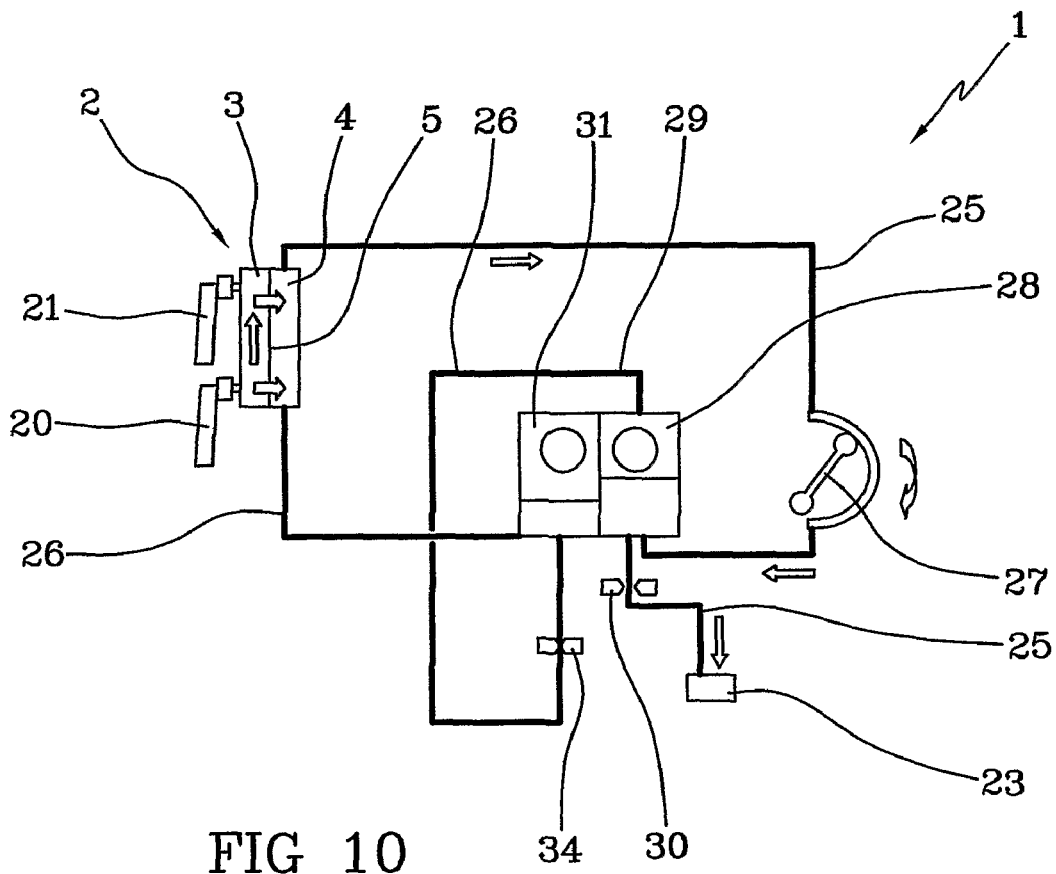

In a fourth stage (FIG. 10) the configuration of FIG. 8 is set up again, i.e. with the blood pump 27 rotating in reverse direction, the venous clamp 34 closed and the arterial clamp 30 open. Following this discharge stage there is a further recirculation stage, as in FIG. 9. Various alternating cycles, discharge and recirculating, can be run, until the air in the extracorporeal circuit 1 is removed and replaced, in the desired quantity, by the filling liquid coming from the fluid chamber 3.

In a further embodiment of the invention, the priming process comprises an adjustment process of the levels in the expansion chambers 28 and 31, comprising a first stage of generating, in the extracorporeal circuit 1, a first predetermined pressure $P_1$, lower than atmospheric pressure (for example $P_1$=–250 mmHg), while the fluid chamber 3 is isolated from the treatment liquid supply line 7 to prevent backfiltering, and a second stage, subsequent to the first stage, in which the pressure in the extracorporeal circuit 1 is increased from the first predetermined pressure $P_1$ to a second predetermined pressure $P_2$ (for example $P_2$=0, i.e. equal to atmospheric pressure), while the fluid chamber 3 is in communication with the supply line of the treatment liquid 7 to allow backfiltering.

In greater detail, during the first depressurisation stage the aspiration device 24 generates a predetermined negative pressure $P_1$ (–250 mmHg) in the extracorporeal circuit so that a part of the filling liquid and the air contained in the circuit are evacuated through the connector 23. During this fluid evacuation stage the fluid chamber 3 of the device 2 is isolated from the dialysis liquid circuit so that the backfiltering of liquid across the membrane is zero; to this end the first bypass line 17 is opened and the check valve 19 is closed. By doing this the aspiration device 24 reduces the pressure in the extracorporeal circuit and extracts a part of the fluids from the extracorporeal circuit without recalling the liquid from the fluid chamber 3 through the membrane of the device 2. In this first stage of the level adjustment process in the expansion chambers 28 and 31, the liquid level in the chambers is lowered to zero. During this depressurisation stage the filling fluid is evacuated from the expansion chambers 28 and 31, and the part of extracorporeal circuit which is comprised between the chambers 28 and 31 and which does not pass through the blood chamber 4, as well as the part of extracorporeal circuit which is comprised between the connection 23 and the nearest expansion chamber and which is therefore directly connected to the aspiration device 24. The quantity of the filling liquid that remains in the extracorporeal circuit is, at the end of this depressurisation stage, known. The negative pressure $P_1$ at which the depressurisation stops is determined in such a way that a quantity of air remaining in the extracorporeal circuit is exactly the quantity needed so that in the following stage the liquid levels reached in the chambers are those desired (as will be better explained herein below). The predetermined negative pressure $P_1$ is predetermined, among other things, on the basis of internal volume in the extracorporeal circuit, as well as on the basis of the liquid levels and the pressure desired in the chambers 28 and 31 at the end of the priming. This first stage of reducing the pressure in the extracorporeal circuit by extraction of fluids is followed by a second stage in which the pressure in the extracorporeal circuit is increased and brought to a second predetermined value $P_2$, for example zero (i.e. atmospheric pressure). This second stage comprises placing the fluid chamber 3 of the device 2 in communication with the treatment liquid circuit: this communication is opened via the closure of the first bypass line 17; the closure is achieved by adjusting the three-way valve arranged on the line 17. By effect of this communication, a certain quantity of liquid passes by backfiltering from the fluid chamber 3 to the blood chamber 4; consequently a certain quantity of liquid enters the venous expansion chamber 31, when the circuit pressure reaches a predetermined intermediate pressure $P_{int}$ (for example –125 mmHg) the blood pump 27 is activated in the rotation direction corresponding to the liquid circulation towards the arterial expansion chamber 28, so as to introduce liquid into this chamber 28; the blood pump 27 is stopped when the pressure in the extracorporeal circuit reaches atmospheric pressure $P_2$ (0 mmHg). In this situation the liquid levels in the chambers 28 and 31 are automatically adjusted to the desired values. The regulation of the liquid levels in the chambers 28 and 31 depends on the choice of pressure values $P_1$, $P_{int}$, and $P_2$. The pressure $P_2$ is selected to be zero in order to prevent dripping or backflow by and in the circuit during the subsequent patient connecting-up stage. The pressure $P_1$ is selected according to the volume of air (known) contained in the extracorporeal circuit at pressure $P_1$ and the volume of air (desired) contained at pressure $P_2$. The pressure $P_{int}$ is selected in such a way that the distribution between the two chambers 28 and 31 of the total volume or air (desired) at pressure $P_2$ is right for obtaining the desired level in each chamber. In other words, the negative pressures $P_1$ and $P_{int}$ generated during the level adjustment process are predetermined—by means of calculations which take account, among other things, of the volume and conformation of the expansion chambers and the desired final pressure $P_2$—so that the levels determined in chambers 28 and 31, once pressure $P_2$ has been re-established (i.e. atmospheric pressure) effectively correspond to those desired. The determination of the negative pressures $P_1$ and $P_{int}$ can be made by calculations or by empirical means.

The above-described process for adjusting the levels can be performed as a final stage of the priming process, or in an intermediate stage, and is applicable both to the process described with reference to FIGS. from 1 to 5 and to the process described with reference to FIGS. from 6 to 10.

An advantageous aspect of the invention is that at the end of the priming process, before connecting the extracorporeal blood circuit to the patient, the circuit itself is, as described, at atmospheric pressure, so that, when the patient end of the arterial line is detached from the service line of the venous expansion chamber, there is no liquid dripping phenomenon from the circuit to the outside, nor is there a backflow of air from the outside environment to the circuit.

Legend:
1. Extracorporeal blood circuit
2. Blood treatment device (dialyser filter)
3. Device 2 fluid chamber
4. Device 2 blood chamber
5. Device 2 semipermeable membrane
6. Treatment liquid preparation circuit (dialysis and/or replacement liquid)
7. Treatment liquid supply line
8. Treatment liquid preparation device
9. First circulation pump or treatment liquid supply pump
10. First flowmeter
11. Filter
12. Filter 11 first chamber
13. Filter 11 second chamber
14. Treatment liquid drainage line 15. Second circulation pump or treatment liquid drainage pump
16. Second flowmeter
17. First bypass line
18. Second bypass line
19. Check valve
20. Connection to inlet of fluid chamber 3
21. Connection to outlet of fluid chamber 3
22. Auxiliary line for excess air and liquid discharge from circuit 1 to circuit 6.
23. Auxiliary connector for connection of the circuit 1 to line 22
24. Aspiration device on line 22
25. Arterial blood line
26. Venous blood line
27. Blood pump
28. Arterial expansion chamber
29. Service lines to the chamber 28
30. Arterial clamp
31. Venous expansion chamber
32. Service line to the chamber 31
33. Air sensor
34. Venous clamp
35. Infusion device

The invention claimed is:

1. A process for filling and/or rinsing an extracorporeal blood circuit, comprising stages of:
providing a blood treatment device having a fluid chamber and a blood chamber which chambers are separated from one another by a semipermeable membrane;
connecting an inlet of the fluid chamber to a supply line of a treatment liquid;
providing an extracorporeal blood circuit having a first blood line and a second blood line, each blood line having a patient end and a device end;
connecting the device ends of the first blood line and the second blood line to the blood chamber;
connecting the patient end of the first blood line to an intermediate zone of the second blood line;
connecting the patient end of the second blood line to a discharge;
circulating a filling and/or rinsing liquid through the membrane of the fluid chamber to the blood chamber and from the blood chamber along at least a part of the extracorporeal circuit up to the discharge,
wherein the stage of connecting the patient end of the first blood line to an intermediate zone of the second blood line comprises connecting the patient end of the first blood line to a service line connected to the upper part of an expansion chamber of the second blood line.

2. The process of claim 1, comprising a stage of connecting the extracorporeal circuit to a reversible blood pump.

3. The process of claim 2, wherein the stage of connecting the extracorporeal circuit to a reversible blood pump comprises connecting the first blood line to the reversible blood pump.

4. The process of claim 2, wherein the stage of connecting the extracorporeal circuit to a reversible blood pump comprises connecting one of the two blood lines to the blood pump, and wherein the stage of circulating a filling and/or rinsing liquid along at least a part of the extracorporeal circuit up to the discharge comprises circulating the filling and/or rinsing liquid through an expansion chamber arranged on the extracorporeal circuit between the blood pump and the patient end of the blood line connected to the blood pump.

5. The process of claim 2, wherein the stage of connecting the extracorporeal circuit to a reversible blood pump comprises connecting one of the two blood lines to the blood pump, and wherein the device end of the blood line connected to the blood pump is connected to a connection of the blood chamber which connection of the blood chamber is located superiorly therein.

6. The process of claim 1, wherein the filling and/or rinsing liquid is circulated in a first circulation direction along a pathway which comprises, in order, the membrane, the blood chamber, the first blood line up to an intermediate zone of the second blood line, and a tract of the second blood line between the intermediate zone and the discharge.

7. The process of claim 6, wherein the filling and/or rinsing liquid is circulated in a second circulation direction along a pathway that comprises, in order, an expansion chamber arranged on the first blood line, a tract of first blood line, connected to the blood pump, the blood chamber, the second blood line and the discharge.

8. The process of claim 1, wherein the filling and/or rinsing liquid is circulated in a first circulation direction along a pathway that comprises, in order, the membrane, the blood chamber and the second blood line up to the discharge, the first blood line being blocked during the circulation in the first circulation direction.

9. The process of claim 8, wherein the filling and/or rinsing liquid is circulated in a second circulation direction along a closed circuit which comprises, in order, the blood chamber, the first blood line up to the intermediate zone of the second blood line, and a tract of the second blood line between the intermediate zone and the device end, a tract of the second blood line between the intermediate zone and the discharge being blocked during the circulation in the second circulation direction.

10. The process of claim 7, wherein the stages of circulating the filling and/or rinsing liquid in a first and in a second circulation direction are made alternatedly and repeatedly.

11. The process of claim 1, comprising further stages of:
generating a first predetermined pressure in the extracorporeal circuit, while the circulation of liquid through the membrane of the fluid chamber to the blood chamber is annulled or prevented, for example by isolating the fluid chamber from the treatment liquid supply line;
increasing the pressure in the extracorporeal circuit from the first predetermined pressure to a second predetermined pressure, greater than the first predetermined pressure, while the circulation of liquid across the membrane from the fluid chamber of the blood chamber is allowed, for example by connecting the fluid chamber to the treatment liquid supply line.

12. The process of claim 11, wherein the second predetermined pressure is equal to atmospheric pressure.

13. A process for filling and/or rinsing an extracorporeal blood circuit, comprising stages of:
providing a blood treatment device having a fluid chamber and a blood chamber which chambers are separated from one another by a semipermeable membrane;
connecting an inlet of the fluid chamber to a supply line of a treatment liquid;
providing an extracorporeal blood circuit having a first blood line and a second blood line, each blood line having a patient end and a device end;
connecting the device ends of the first blood line and the second blood line to the blood chamber;
connecting the patient end of the first blood line to an intermediate zone of the second blood line;
connecting the patient end of the second blood line to a discharge;

circulating a filling and/or rinsing liquid through the membrane of the fluid chamber to the blood chamber and from the blood chamber along at least a part of the extracorporeal circuit up to the discharge;

connecting the extracorporeal circuit to a reversible blood pump;

wherein the stage of connecting the extracorporeal circuit to a reversible blood pump comprises connecting one of the two blood lines to the blood pump, and wherein the stage of circulating a filling and/or rinsing liquid along at least a part of the extracorporeal circuit up to the discharge comprises circulating the filling and/or rinsing liquid through an expansion chamber arranged on the extracorporeal circuit between the blood pump and the patient end of the blood line connected to the blood pump.

14. A process for filling and/or rinsing an extracorporeal blood circuit, comprising stages of:

providing a blood treatment device having a fluid chamber and a blood chamber which chambers are separated from one another by a semipermeable membrane;

connecting an inlet of the fluid chamber to a supply line of a treatment liquid;

providing an extracorporeal blood circuit having a first blood line and a second blood line, each blood dine having a patient end and a device end;

connecting the device ends of the first blood line and the second blood line to the blood chamber;

connecting the patient end of the first blood line to an intermediate zone of the second blood line;

connecting the patient end of the second blood line to a discharge;

circulating a filling and/or rinsing liquid through the membrane of the fluid chamber to the blood chamber and from the blood chamber along at least a part of the extracorporeal circuit up to the discharge;

wherein the filling and/or rinsing liquid is circulated in a first circulation direction along a pathway that comprises, in order, the membrane, the blood chamber and the second blood line up to the discharge, the first blood line being blocked during the circulation in the first circulation direction.

15. The process of claim 14, wherein the filling and/or rinsing liquid is circulated in a second circulation direction along a closed circuit which comprises, in order, the blood chamber, the first blood line up to the intermediate zone of the second blood line, and a tract of the second blood line between the intermediate zone and the device end, a tract of the second blood line between the intermediate zone and the discharge being blocked during the circulation in the second circulation direction.

* * * * *